_United States Patent_ [19]

Norman

[11] Patent Number: 4,485,665

[45] Date of Patent: Dec. 4, 1984

[54] DETECTION OF TOXIC VAPORS

[75] Inventor: J. James Norman, Ottawa, Canada

[73] Assignee: Minister of National Defence of her Majesty's Canadian Government, Ottawa, Canada

[21] Appl. No.: 663,207

[22] Filed: Mar. 1, 1976

[30] Foreign Application Priority Data

May 6, 1975 [CA] Canada .................................. 226384

[51] Int. Cl.² .............................................. G01N 7/04
[52] U.S. Cl. ............................................ 73/19; 73/23;
422/56; 422/87; 436/181
[58] Field of Search ................ 73/19, 23, 24, 421.5 R,
73/863.41; 23/232 R, 254 R; 422/56, 87;
436/181

[56] References Cited

U.S. PATENT DOCUMENTS

| | | | |
|---|---|---|---|
| 2,662,393 | 12/1953 | Rzasa | 73/23 |
| 3,166,938 | 1/1965 | Weyrauch et al. | 73/23 X |
| 3,451,901 | 6/1969 | Seiger et al. | 23/232 R X |
| 3,507,622 | 4/1970 | Tammelin et al. | 73/23 X |
| 3,628,915 | 12/1971 | Robertson | 23/232 R X |
| 3,699,814 | 10/1972 | Kaufman | 73/421.5 R |

_Primary Examiner_—Richard D. Lovering

_Attorney, Agent, or Firm_—Stevens, Davis, Miller & Mosher

[57] ABSTRACT

An improved apparatus is provided for detecting the presence of small concentrations of one gas, e.g. a poisonous or other noxious gas, in another gas, e.g. air. The gaseous mixture, e.g. contaminated air is caused to contact a colorimetric detector, e.g., an enzyme, supported on or in a support surface. The improvement involves having a sampling head for the vapor detection apparatus including (a) a detection chamber; (b) an opening permitting the insertion of a vapor detector into the detection chamber; (c) an inlet to the detection chamber, such inlet including a critical orifice directed towards the detection chamber; (d) an outlet from the detection chamber; (e) an interrelated coordination of the orifice diameter and the pressure drop across the orifice to cause a gas to pass through the critical orifice at a jet stream velocity approaching the velocity of sound, at that temperature (f) a vapor detector adapted to be positioned in the detection chamber via the opening (b), and (g) an air by-pass interconnecting the inlet and the outlet such that, in operation most of the air stream is directed from the critical orifice against, but not through the detector, and through the air by-pass through the outlet.

21 Claims, 15 Drawing Figures

DETECTION OF TOXIC VAPORS

BACKGROUND OF THE INVENTION (i) Field of the Invention

This invention relates to method and apparatus for detecting vapours of one gas in another gas. More particularly, it is directed to method and means for detecting toxic or other noxious gases in air.

(ii) Description of the Prior Art

There is presently a need to detect vapours of chemical warfare agents (particularly vapours of the "so-called" G. and V-agents) in air down to very low concentrations. To be useful in the field, such detection should be made rapidly, i.e. taking no more than 10 minutes, and should be made using a simple apparatus which can be easily carried and used by untrained soldiers in the field.

There are two ways for detecting such vapours in air. The first involves the detection of the presence of dangerous concentrations of vapours of the agent. The second involves the detection of the absence of dangerous concentrations of vapours of the agent. In the first way, the test is used to provide a positive indication of concentrations producing militarily significant effects down to the threshold level, as well as to provide a readily recognizable negative indication of lower concentrations. In the second way, the test is used to provide a positive indication of concentrations lower than those producing militarily significant effects, as well as to provide a readily recognizable negative indication of higher concentrations.

As used in the present specification, the term "militarily significant effects" is intended to mean the developement, in a small fraction (1–5%) of exposed personnel, of no more than mild symptoms of poisoning by the agent. The appearance of such mild symptoms is related to the rate at which agent enters the body. This is a function of the breathing rate, the vapour concentration, and the body collection efficiency. The requirement is for detection of concentrations which do not exceed the above criteria of casuality production in resting or mildly active men exposed for an indefinite time. This indefinite time may be further defined as 12 hours.

Means for detection of such vapours in air which are currently available involve the provision of a bibulous material (e.g. absorbent paper) impregnated with a colorimetric agent, e.g. an enzyme which reacts with the particular agent being detected to provide a colour indication. The precise nature of such colorimetric agent is not important since it has no bearing on the present invention. However, in general, it can be said that in one such chemical system, contact between the impregnated bibulous material (e.g. paper) and air results either in the development of colour (absence of agent), or no development of colour (presence of agent) on the paper. In another such chemical system, contact between the impregnated bibulous material (e.g. paper) and air results in colour being developed very rapidly. If this colour persists for more than 2 minutes, agent is present, if the colour fades to white within the 2 minute period, agent is absent.

Contact between the air and the bibulous material may be achieved either by pulling an air sample therethrough with a handpump, or by waving the detector (i.e. the impregnated paper) in the air.

All the above means will detect low concentrations of the vapours of the agents but their sensitivities are not adequate. To detect the very much lower concentrations which do not produce symptoms after 12 hour exposure, the techniques of quantitative analysis must be employed. Such techniques are complicated and time-consuming. In addition, they must be performed by a trained analyst. Such approaches, therefore, are unsuited for field use.

SUMMARY OF THE INVENTION (i) Aims of the Invention

It is therefore, an object of this invention to provide a novel method for increasing the sensitivity of the tests using the above-described impregnated papers.

Another object of this invention is to provide novel apparatus for the detection of noxious or poisonous vapours in gases.

(ii) Statement of the Invention

It has now surprisingly been found that the sensitivity of the test may be increased by approximately two orders of magnitude by generating an air jet stream by means of an orifice operating under critical conditions, i.e. when the orifice diameter (or area) is sufficiently small and the pressure drop across the orifice is sufficiently large, so that the jet stream velocity is a function only of the gas viscosity and its temperature and approaches the maximum possible value, namely, the velocity of sound in air at the temperature, and directing such air against the vapour detecting element.

This invention provides an improved vapour detection apparatus including a sampling head having a main body portion including: (a) a detection chamber; (b) means for the insertion of a vapour detector into the detection chamber; (c) inlet means to the detection chamber, such inlet means including a critical orifice directed towards the detection chamber; (d) outlet means from the detection chamber; (e) means for causing a gas to pass through the critical orifice at a jet stream velocity approaching the velocity of sound in the gas at that temperature by co-ordinating the orifice diameter and the pressure drop across the orifice; (f) a vapour detector adapted to be positioned in the detection chamber via the insertion means; and (g) an air by-pass means interconnecting the inlet means and the outlet means such that, in operation, most of the air stream is directed from the critical orifice against, but not through, the detector, and through the air by-pass means to the outlet means. The detection chamber in the main body portion may be provided in a single integral unit, or it may be provided between two hingedly connected parts with the gas inlet means (c) in one part, and the gas outlet means (d) in the other part, or it may be provided as a recess between the main body portion and a cap detachably secured thereto.

This invention provides, still further a one piece sampling head including a generally cylindrical body provided with a sampling chamber; a slotted inlet provided with a self-sustaining vapour detection element disposed in the sampling chamber; an inlet to the sampling chamber; and outlet from the sampling chamber; means for connecting the outlet from the sampling chamber to a pump for drawing a gas therethrough; and a nozzle disposed in the inlet to the sampling chamber, the nozzle having a critical orifice to accelerate the gas passing therethrough to a velocity approaching the velocity of sound in that gas.

This invention, provides, still further a two piece sampling head, comprising a pair of hinged plates; a sampling chamber recessed in the plates within facing surfaces thereof; a slotted inlet to the sampling chamber, the inlet being provided with a self-sustaining vapour detection element disposed in the sampling chamber; sealing gasket means disposed against one face of the vapour detection element; an inlet nozzle to the sampling chamber, the nozzle having a critical orifice to accelerate the gas passing therethrough to a velocity approaching the velocity of sound in that gas; an outlet from the sampling chamber; and means for connecting the outlet from the sampling chamber to a pump for drawing gas therethrough.

This invention also provides a two piece head including a generally cylindrical externally threaded body and an internally threaded cylindrical cap operatively associated therewith, and defining, therebetween, a sampling chamber; a slotted inlet provided with a self-sustaining vapour detection element disposed in the sampling chamber; a pair of O-ring gasket members contacting the vapour detection element to provide an air tight sampling chamber; an inlet to the sampling chamber; and outlet from the sampling chamber; means for connecting the outlet from the sampling chamber to a pump for drawing gas therethrough; and a nozzle disposed on the inlet to the sampling chamber, the nozzle having a critical orifice to accelerate the gas passing therethrough to a velocity approaching the velocity of sound in that gas.

In variants of all of these embodiments, the vapour detection apparatus may comprise a self-sustaining element; an inset aperture formed therethrough; and a bibulous element impregnated with a suitable vapour detection element covering one face of the inset aperture.

Figure 1:
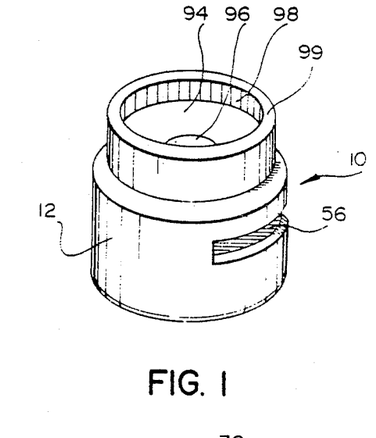
FIG. 1 is an isometric view, seen from above, of the sampling head according to one embodiment of the present invention.
Figure 2:
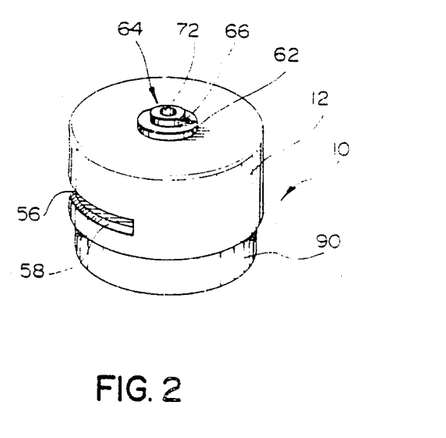
FIG. 2 is an isometric view, seen from below, of the sampling head of FIG. 1.
Figure 3:
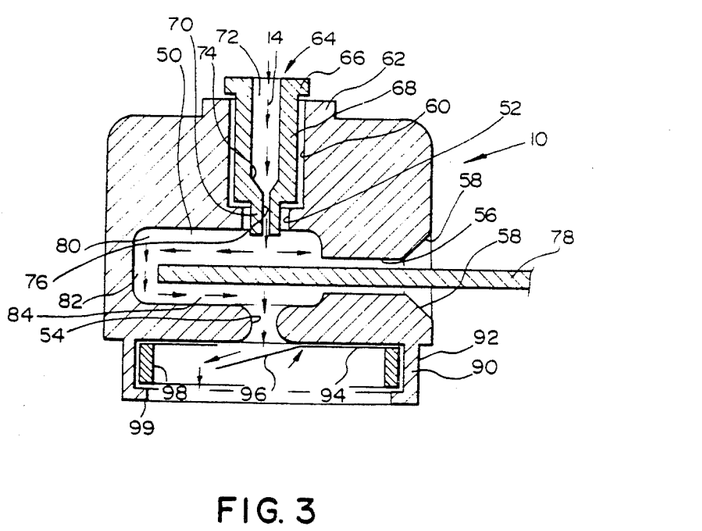
FIG. 3 is a central vertical cross-section through the sampling head of FIG. 1.
Figure 4:
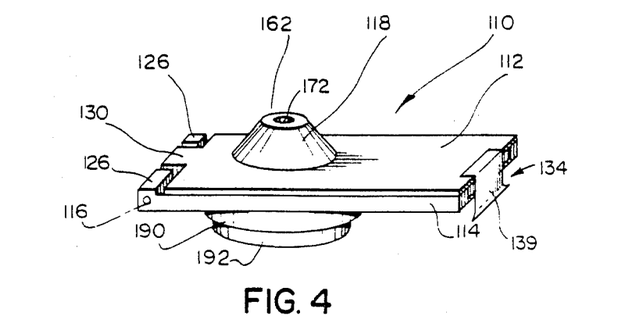
FIG. 4 is an isometric view, seen from above, and in its closed position, of a sampling head according to a second embodiment of the present invention.
Figure 5:
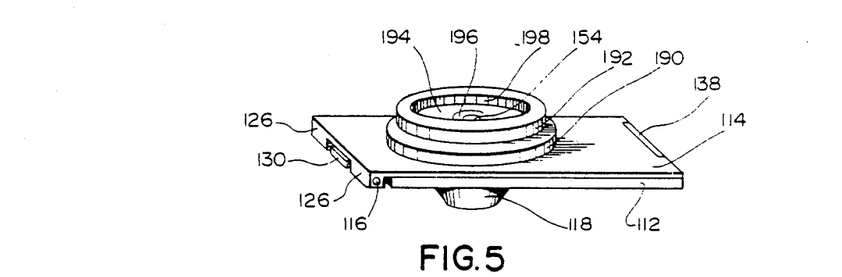
FIG. 5 is an isometric view, seen from below, of the sampling head of FIG. 4.
Figure 6:
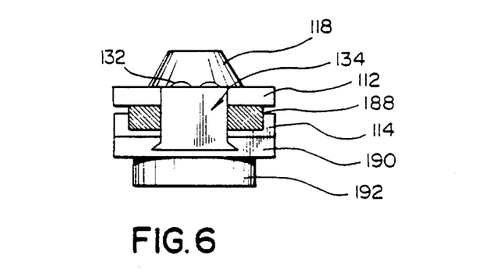
FIG. 6 is a front elevational view of the sampling view of the sampling head of FIG. 4.
Figure 7:
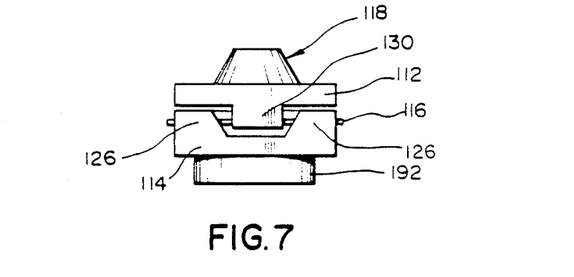
FIG. 7 is a rear elevational view of the sampling head of FIG. 4.
Figure 8:
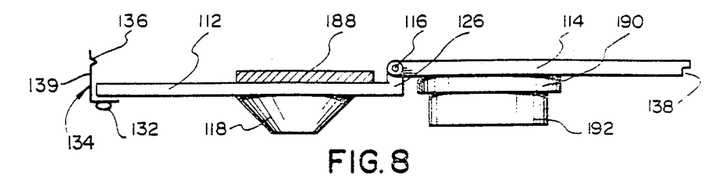
FIG. 8 is a side elevational view of the sampling head of FIG. 4, in its open position.
Figure 9:
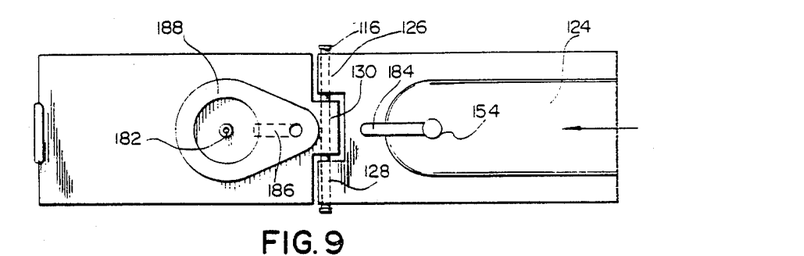
FIG. 9 is a plan view of the sampling head of FIG. 8, viewed from above.
Figure 10:
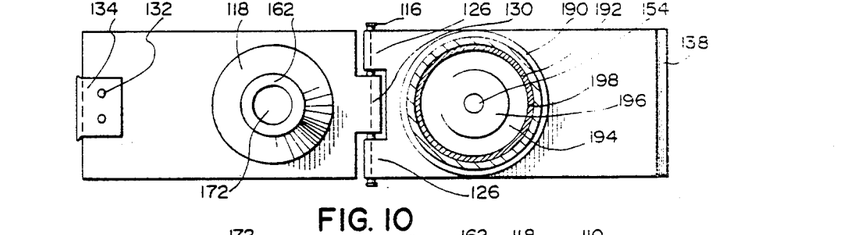
FIG. 10 is a plan view of the sampling head of FIG. 8, viewed from below.
Figure 11:
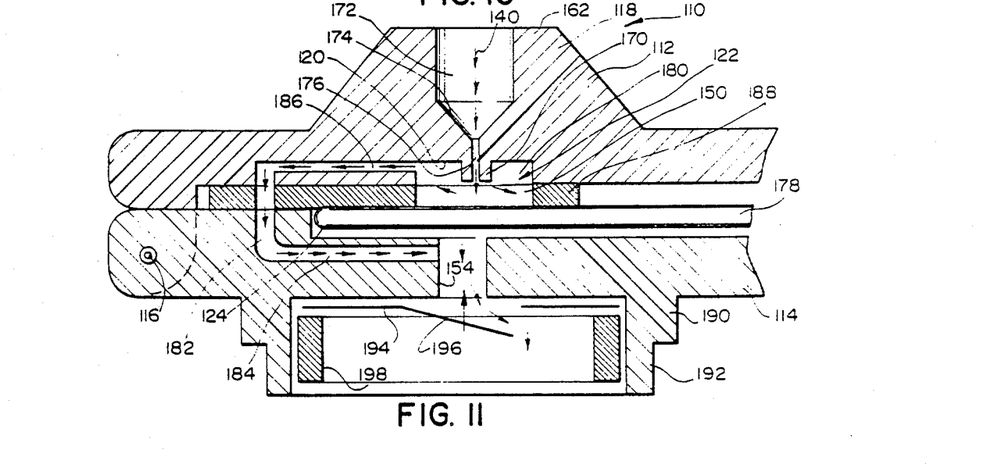
FIG. 11 is a central vertical and longitudinal cross-sectional view of the sampling head of FIG. 4.

DESCRIPTION OF PREFERRED EMBODIMENTS (i) Description of the Embodiment of FIGS. 1 to 3

Before describing the structure and operation of embodiments of this invention, it is desired to emphasize that the most common gas in which a noxious gas may be present is air, and so the description will refer to the use of air.

As seen in FIGS. 1 to 3, one embodiment of this invention is in the form of a sampling head indicated generally by reference numeral 10 including a main upper cylindrical body portion 12. The main body portion 12 is provided with an internal detection chamber 50, having an inlet port 52, an outlet port 54 and a lateral entry slot 56 having upper and lower chamfered edges 58 for the insertion and removal of the gas detection element. Inlet port 52 emerges from an enlarged bore 60 which is surrounded by a terminal, raised upper annular support shoulder 62. Disposed within bore 60 is a nozzle indicated generally as 64 and including an upper annular support flange 66, a main cylindrical portion 68 and a tip 70 projecting through inlet port 52. Nozzle 64 is provided with a main bore 72 and a tapering frusto-conically shaped bore 74, leading to a critical orifice opening 76 of smaller diameter.

A vapour detector element 78, generally in the form of a bibulous strip impregnated with the detector element, is disposed in the detection chamber 50 through the entry slot 56, to divide the chamber 50 into an upper contact channel 80, a lateral bypass channel 82, and an outlet channel 84, communicating with outlet port 54. Sealing means (not shown) at the mouth of the slot 56 should be provided in order to provide for air-sealing of the chamber 50.

Integral with the lower portion of upper body 12 is a depending hollow cylinder 90 provided with an outer surface 92 acting as an engagement fitting. A circular rubber disc 94 provided with a central flap valve 96 is held in place by means of a retaining ring 98, secured within cylinder 90 by an inwardly directed annular retaining flange 99.

In one embodiment of this aspect of this invention, the main body 12 was molded from rubber and carried a critical orifice unit or nozzle 64 which may be fabricated from brass, nylon, or Teflon (the Trade Mark for a polytetrafluoroethylene).

(ii) Description of the Embodiment of FIGS. 4 to 11

Turning now to a second aspect of this invention, and more particularly to the embodiment of the sampling head shown in FIGS. 4 to 11, it is seen that the sampling head indicated generally by 110 includes an upper generally rectangular plate-like body portion 112 and a lower generally rectangular plate-like body portion 114, hingedly interconnected by mutually mortised ends connected by hinge pin 116.

Lower body 114 is provided with a pair of spaced apart upstanding posts 126, each provided with a transverse bore 128, and an upper body 112 is similarly provided with a central complementary depending post 130 also provided with co-operating mating bore 128, thus providing the mutually mortised ends. Hinge pin 116 hingedly secures upper body 112 and lower body 114 together by passing through the bore 128.

Secured to the upper face of the upper body 112 by pins 132 is a spring clip shown generally as 134 including a vertical portion 139 having a retaining projection 136 thereon. The bottom edge of lower body 114 is provided with a retaining recess 138.

Upper body portion 112 is provided with an integral, raised frusto-conical protuberance 118, terminating in an upper shoulder 162. A central bore 172 is provided within protuberance 118, converging frusto-conically to bore 174 to terminate in critical orifice 176. Orifice 176 extends through tip 170 which integrally depends from the roof 120 of a recess 122 in body portion 112. A portion of recess 122 forms the upper contact channel 180 of the detection chamber 150.

A vapour detector element 178 generally in the form of a bibulous strip impregnated with a suitable detector element is disposed in the portion of the detection chamber 150 defined by recess 124 in the lower body portion 114. Recess 124 communicates with the outlet port 154. A portion of the upper recess 122 of detection chamber 150 constitutes an upper contact channel 180 and an upper bypass channel 186, which comm nicates with a lateral bypass channel 182 which, in turn, communicates with an outlet channel 184. Sealing means, in the form of a suitably apertured oblong gasket 188, is disposed between upper body 112 and lower body 114. Additional sealing means should be provided at the entrance to the recess 124 to assure airtight sealing between the recess 124 and the vapour detector element 178.

Integral with the bottom of the lower body 114 is a depending cylinder 190 provided with a stepped outer surface 192 acting as an engagement fitting. A circular rubber disc 194 provided with a central circular flap valve 196 is held in place by means of a retaining ring 198 disposed within the interior of cylinder 190.

The sampling head of this embodiment of this aspect of this invention was fabricated entirely from nylon.

Figure 12:
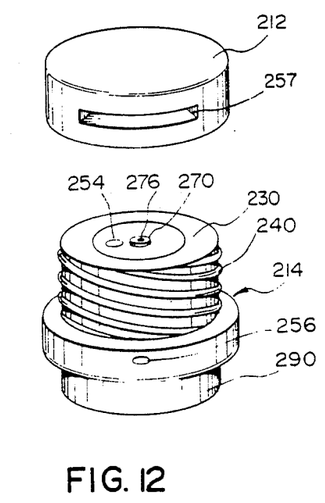
FIG. 12 is an exploded isometric view, seen from above, of a sampling head according to a third embodiment of this invention.
Figure 13:
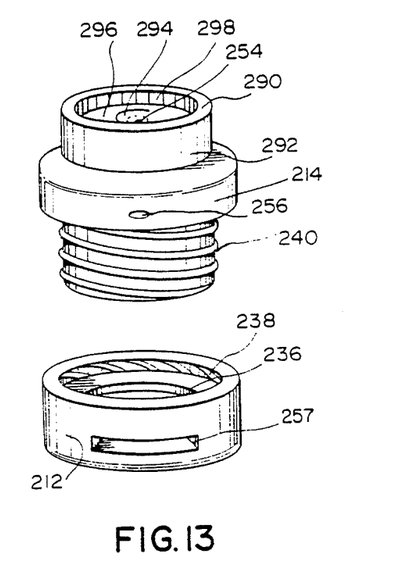
FIG. 13 is an exploded isometric view, seen from below, of the sampling head of FIG. 12.
Figure 14:
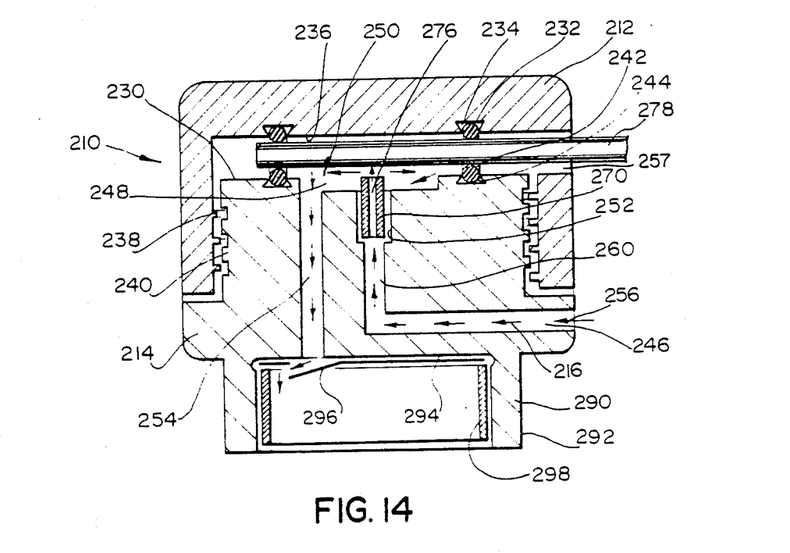
FIG. 14 is a central vertical cross-sectional view of the sampling head of FIG. 12, in assembled form.

(iii) Description of the Embodiments of FIGS. 12 to 14

As seen in FIGS. 12 to 14, a third embodiment of this invention is in the form of a sampling head 210 including a lower cylindrical body 214, and an upper cap 212. Lower cylindrical body 214 is provided with a recess 248 defining an internal detection chamber 250 having an axial inlet port 252 and an axial outlet port 254. Disposed in inlet port 252 is a cylindrical nozzle 270, the outlet bore 276 of which constitutes a critical orifice opening. An axial well 260 communicates inlet port 254, with radial inlet bore 246 for the admission of air through inlet port 256 to the sampling head 210.

The upper face 230 of the lower cylindrical body 214 is provided with an annular recess 244, within which is disposed an O-ring gasket 242. The outer cylindrical surface of body 214 is provided with helical threads 240.

Upper cap 212 is provided with internal helical threads 238, and with a radial slot 257. The inner surface 236 of cap 212 is provided with an annular recess 234 within which is disposed an O-ring gasket 232.

A vapour detector element 278 generally in the form of a bibulous strip impregnated with a suitable detector element is disposed in the detection chamber 250 through the radial slot 257. Air discharged through critical orifice 276 passes into an upper contact channel 250 and then through a lateral bypass channel and then out through outlet port 254. The pair of O-ring gaskets 242, 232 are provided in order to provide air-tight entry of element 278 into chamber 250.

Integral with the lower portion of body 214 is a depending cylinder 290 provided with an outer surface 292 acting as an engagement fitting. A circular disc 294 provided with a central circular flap valve 294 is held in place by means of a retaining ring 298 disposed within cylinder 290.

The sampling head of this embodiment of this aspect of this invention was fabricated from nylon and carried a nylon critical orifice unit or nozzle 270.

Figure 15:
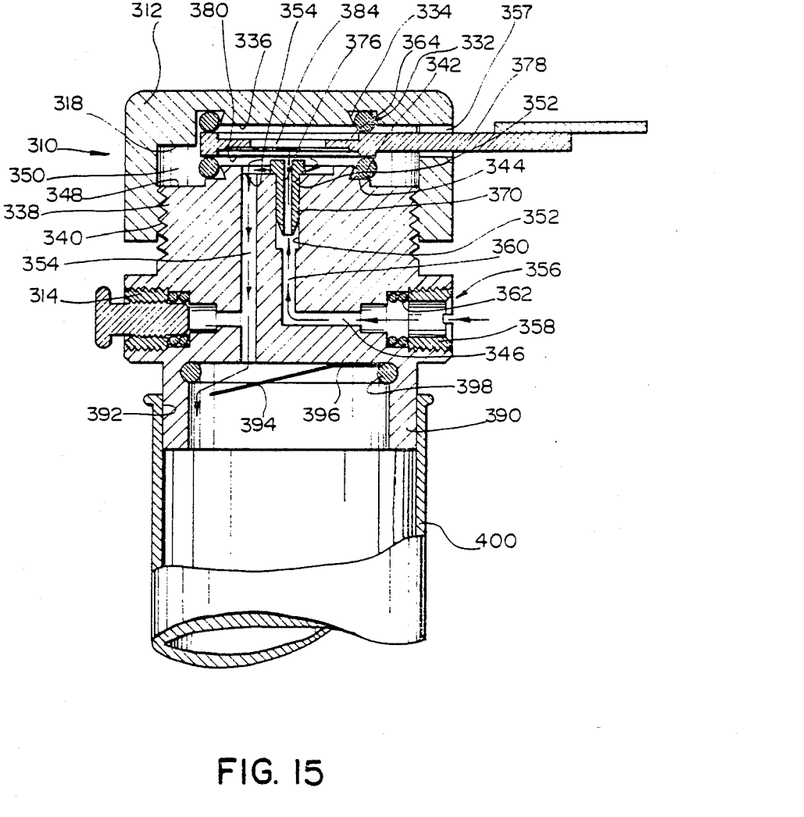
FIG. 15 is a central vertical cross-sectional view of the gas detection device of yet another aspect of this invention.

(iv) Description of the Embodiment of FIG. 15

As seen in FIG. 15, a fourth embodiment of this invention is seen in the form of a sampling head 310 including a lower, generally cylindrical lower body 314 and an upper cap 312. The lower body 314 is provided with an annular recess 348 which, together with a similar recess 318 in the upper cap 312, provides an internal detection chamber 350, having an axial inlet port 352 and an axial outlet port 354. Disposed in inlet port 352 is a generally cylindrical nozzle 370, the bore of which constitutes a critical orifice opening. An axial well 360 communicates between inlet port 352 and radial inlet bore 346 to provide for the admission of air to be tested to the sampling head 310. Inlet bore 346 is provided with inlet port 356 in which is fitted internal connecting plug 358, sealed therein with O-rings 362.

The upper face of the lower body 314 is provided with a central cylindrical recess 364, embracing inlet port 352 and outlet port 354. The upper face of the lower cylindrical body is also provided with an annular recess 344, within which is disposed an O-ring gasket 342. The outer cylindrical surface of body 314 is provided with external threads 338.

Upper cap 312 is provided with internal threads 340, cooperating with threads 338 on body 314, and a radial inlet slot 357. The inner surface 336 of cap 312 is provided with an annular recess 334 within which is disposed an O-ring gasket 332.

A vapour detector element 378 is disposed in detection chamber 350 through radial inlet slot 357. Vapour detector element 378 is generally in the form of a self-sustaining member provided with an inset and circular window 384, which is closed by a detecting element, namely a bibulous element impregnated with a detector substance, e.g. an enzyme. Air discharged through critical orifice 376 passes into an upper sealed contact channel 380, and then down through outlet port 354. The pair of O-ring gaskets 342, 332 disposed between body 314, vapour detector element 378 and cap 312 provides for a sealing of the air within contact channel 380.

Integral with the lower portion of body 314 is a depending cylinder 390 provided with an outer surface 392 acting as an engagement fitting for the main tube 400 of a hand pump. A circular resilient disc provided with a central flap is held in place by means of an O-ring 398 disposed within cylinder 390.

OPERATION OF PREFERRED EMBODIMENTS (i) Operation of the Embodiment of FIGS. 1 to 3

In use, the sampling head is attached to the air inlet of a handpump (not shown) by means of engagement of the air inlet with the outer surface 92 of the depending hollow cylinder 90. The handpump is operated so as to draw air through the main bore 72 by the automatic opening of the one-way flap valve 96. The air moves in the direction of the arrows 14 and the jet stream velocity at the outlet of the critical orifice 76 is increased to the maximum value approaching the velocity of sound. Part of the air passes through the porous vapour detector 78 and out the outlet port 54. Most of the air, however, passes through the upper contact channel 80, the lateral bypass channel 82 and the outlet channel 84. After a suitable period of time, i.e. of the order of 5-10 minutes, the operation of the handpump is stopped, and the vapour detector 78 is removed and examined in the usual manner, well known to those skilled in the art.

(ii) Operation of the Embodiment of FIGS. 4 to 11

In use, the vapour detector 178 is placed on recess 124 and the upper body 112 hingedly placed over the lower body 114 and the two halves held together with spring clip 134, recess 124 is preferably air-tight now. Then, the sampling head 110 is attached to the air inlet of a handpump (not shown) by means of engagement of the air inlet with the outer surface 192 of the depending hollow cylinder 190. The handpump is operated so as to draw air through the main bore 172 by the automatic opening of the one-way flap valve 196. The air moves in the direction of the arrows 140 and the jet stream velocity at the outlet of the critical orifice 176 is increased to the maximum value approaching the velocity of sound. Part of the air passes through the porous vapour detector 178 and out the outlet port 154. Most of the air, however, passes through the upper contact channel 180, the upper bypass channel 186, the lateral bypass channel 182 and the outlet channel 184. After a suitable period of time, i.e. of the order of 5 to 10 minutes, the operation of the handpump is stopped, and the vapour detector 178 is removed and examined in the usual manner.

(iii) Operation of the Embodiment of FIGS. 12 to 14

In use, the sampling head 210 is attached to the air inlet of a handpump (not shown) by means of engagement of the air inlet with the outer surface 292 of the depending hollow cylinder 290. The handpump is operated so as to draw air through the main bore 276 by the automatic opening of the oneway flap valve 296. The air moves in the direction of the arrows 216 and the jet stream velocity at the outlet of the critical orifice 276 is increased to the maximum value approaching the velocity of sound. Part of the air passes both ways through the porous vapour detector 278 but most of the air passes through the upper contact channel 250, and then downwardly through the outlet port 254. After a suitable period of time, i.e. of the order of 5 to 10 minutes, the operation of the handpump is stopped, and the vapour detector 278 is removed and examined in the usual manner.

(iv) Operation of the Embodiment of FIG. 15

In use, the sampling head 310 is attached to the air inlet of a handpump 400 by means of engagement of the air inlet with the outer surface 392 of the depending hollow cylinder 390. The handpump is operated so as to draw air down through air outlet 354. This caused air to be drawn in from air inlet 346. The air moves in the direction of the arrows from the inlet 356, through inlet bore 346 and the jet stream velocity at the outlet of the critical orifice 376 is increased to the maximum value approaching the velocity of sound. Part of the air passes through the porous portion of the vapour detector 378. However, the movement of the air caused by the pump 400 drives most of the air through outlet bore 354. After a suitable period of time, i.e. of the order of 5 to 10 minutes, the operation of the handpump is stopped and the vapour detector 378 is removed through the radial inlet slot 357 and examined in the usual manner.

(v) General Description of Operation

The four embodiments of the sampling heads carrying critical orifices described above were attached to a handpump capable of producing the required critical conditions across the orifice. These, when tested, performed satisfactorily, producing sensitivities of the vapour detector approximately two orders of magnitude over the use of the vapour detector without the sampling head. The time required for sampling and testing was approximately 6 minutes. The maximum air sample volume was 4.5 liters.

These embodiments of this invention may be used to tell when it is safe for soldiers to unmask for extended times (at least 12 hours). These sampling heads are small, cheap, simple, and require no training in use and are suitable for use in the field. The time required for testing is short, approximately 6 minutes, and the air volume sampled is small.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications, are properly, equitably and intended to be, within the full range of equivalents of the following claims.

I claim:

1. In a vapour detection apparatus, a sampling head having a main body portion including:
   (a) a detection chamber;
   (b) means for the insertion of a vapour detector into the detection chamber;
   (c) inlet means to the detection chamber, said inlet means including a critical orifice directed towards the detection chamber;
   (d) outlet means from the detection chamber;
   (e) means for causing a gas to pass through the critical orifice at a jet stream velocity approaching the velocity of sound in that gas at that temperature by co-ordinating the orifice diameter and the pressure drop across the orifice;
   (f) a vapour detector adapted to be positioned in said chamber via said insertion means; and
   (g) an air by-pass means interconnecting said inlet means and said outlet means, such that in operation most of the air stream is directed from said critical orifice, against but not through the detector, and through the air by-pass means to said outlet means.

2. The vapour detection apparatus of claim 1 wherein the critical orifice is provided in a separate nozzle secured into the main body portion.

3. The vapour detection apparatus of claim 2 wherein the means (b) for insertion of a vapour detector is a slot communicating with the detection chamber.

4. The vapour detection apparatus of claim 2 wherein the gas is air, and wherein the means (e) for causing the air to pass through the critical orifice is a suction pump, to which the outlet means (d) is connected by detachable fitting means on the main body portion.

5. The vapour detection apparatus of claim 4 including a one-way flap valve associated with the outlet means (d) to permit air to flow outwardly only.

6. The vapour detection apparatus of claim 1 wherein the gas is air and wherein the critical orifice is intergral with the air inlet means to the detection chamber.

7. The vapour detection apparatus of claim 6 wherein the main body is provided as two hingedly connected parts with the air inlet means (c) in one part, and the air outlet means (d) in the other part.

8. The vapour detection apparatus of claim 7 wherein the means (b) for the insertion of the vapour detector is a recess between the two parts of the main body.

9. The vapour detection apparatus of claim 7 including gasket means disposed between the two parts of the main body.

10. The vapour detection apparatus of claim 6 wherein the means (e) for causing the air to pass through the critical orifice is a suction pump, to which the outlet means (d) is connected by detachable fitting means on the main body portion.

11. The vapour detection apparatus of claim 10 including a one-way flap valve associated with the outlet means (d) to permit air to flow outwardly only.

12. The vapour detection apparatus of claim 1, wherein the detection chamber (a) is provided as a recess between the main body portion and a cap detachably secured thereto.

13. The vapour detection apparatus of claim 12 wherein the detection chamber (a) is provided between the body and a vapour detector disposed between the cap and the body and is sealed by gaskets in contact with the body and the vapour detector.

14. The vapour detection apparatus of claim 13 wherein the critical orifice is provided in a separate nozzle into the main body portion.

15. The vapour detection apparatus of claim 14 wherein the means (e) for causing the air to pass through the critical orifice is a suction pump, to which the outlet means (d) is connected by detachable fitting means on the main body portion.

16. The vapour detection apparatus of claim 15 including a one-way flap valve associated with the outlet means (d) to permit air to flow outwardly only.

17. A one piece sampling head for a vapour detection apparatus as claimed in claim 1 in which the gas is air and including a generally cylindrical body provided with a sampling chamber; a slotted inlet provided with a self-sustaining vapour detection element disposed in said sampling chamber; an inlet to said sampling chamber; an outlet from said sampling chamber; means for connecting the outlet from said sampling chamber to a pump for drawing air therethrough; and a nozzle disposed in said inlet to said sampling chamber, said nozzle having a critical orifice to accelerate the air passing therethrough to a velocity approaching the velocity of sound.

18. A two piece sampling head for a vapour detection apparatus as claimed in claim 1, in which the gas is air and including a pair of hinged plates, a sampling chamber recessed in said plates within facing surfaces thereof; a slotted inlet to said sampling chamber, said inlet being provided with a self-sustaining vapour detection element disposed in said sampling chamber; sealing gasket means disposed against one face of said vapour detection element; and inlet nozzle to said sampling chamber, said nozzle having a critical orifice to accelerate the air passing therethrough to a velocity approaching the velocity of sound; and outlet from said sampling chamber; and means for connecting the outlet from said sampling chamber to a pump for drawing air therethrough.

19. A two piece sampling head for a vapour detector apparatus as claimed in claim 1, in which the gas is air and including a generally cylindrical externally threaded body and an internally threaded cylindrical cap operatively associated therewith, and defining, therebetween, a sampling chamber; a slotted inlet provided with a self-sustaining vapour detection element disposed in said sampling chamber; a pair of O-ring gasket members contacting said vapour detection element to provide an air tight sampling chamber; an inlet to said sampling chamber; an outlet from said sampling chamber; means for connecting the outlet from said sampling chamber to a pump for drawing air therethrough; and a nozzle disposed in said inlet to said sampling chamber, said nozzle having a critical orifice to accelerate the air passing therethrough to a velocity approaching the velocity of sound.

20. A two piece sampling head for a vapour detection apparatus as claimed in claim 1, in which the gas is air and including a generally cylindrical externally threaded body and an internally threaded cylindrical cap operatively associated therewith, and defining, therebetween, a sampling chamber; a slotted inlet provided with a self-sustaining vapour detection element disposed in said sampling chamber, said vapour detection element comprising a self-sustaining element; an inset aperture formed therethrough; and a bibulous element impregnated with a suitable vapour detection element covering one face of said inset aperture.

21. The vapour detection apparatus of claim 1, wherein said detector chamber includes a contact channel in which the air stream from the critical orifice is directed against the detector, and a by-pass channel downstream of said detector chamber in fluid communication with said outlet means.

* * * * *